United States Patent
Anderson et al.

(10) Patent No.: US 6,880,722 B2
(45) Date of Patent: Apr. 19, 2005

(54) MEDICAMENT DISPENSER

(75) Inventors: Gregor John McLennan Anderson, Ware (GB); Philip William Farr, Ware (GB); Paul Kenneth Rand, Ware (GB); Stephen James Harvey, Ware (GB)

(73) Assignee: Glaxo Group Limited, Greenford (GB)

( * ) Notice: Subject to any disclaimer, the term of this patent is extended or adjusted under 35 U.S.C. 154(b) by 49 days.

(21) Appl. No.: 10/415,291

(22) PCT Filed: Oct. 19, 2001

(86) PCT No.: PCT/EP01/12107

§ 371 (c)(1),
(2), (4) Date: Jul. 17, 2003

(87) PCT Pub. No.: WO02/36189

PCT Pub. Date: May 10, 2002

(65) Prior Publication Data

US 2004/0099676 A1 May 27, 2004

(30) Foreign Application Priority Data

Oct. 31, 2000 (GB) .............................. 0026647

(51) Int. Cl.$^7$ ............................... B65H 5/28
(52) U.S. Cl. ....................... 221/71; 206/531
(58) Field of Search ................ 221/71, 69, 73, 221/74, 82, 84, 87, 7, 9, 13, 25, 26; 206/531, 532, 533; 128/203.15, 200.14

(56) References Cited

U.S. PATENT DOCUMENTS

| 4,733,797 A | * | 3/1988 | Haber ........................... 221/8 |
| 5,622,166 A | | 4/1997 | Eisele et al. |
| 5,755,218 A | | 5/1998 | Ritson et al. |
| 5,860,419 A | | 1/1999 | Davies et al. |
| 5,921,237 A | | 7/1999 | Eisele et al. |
| 5,971,951 A | | 10/1999 | Ruskewicz |

FOREIGN PATENT DOCUMENTS

| DE | 19855851 | 12/1999 |
| GB | 2240758 | 3/2000 |
| WO | 9834664 | 8/1998 |
| WO | 9927987 | 6/1999 |
| WO | 9947099 | 9/1999 |
| WO | 0043287 | 7/2000 |
| WO | 0126720 | 4/2001 |

* cited by examiner

Primary Examiner—Kenneth Noland
(74) Attorney, Agent, or Firm—James P. Riek

(57) ABSTRACT

There is provided a medicament dispenser for dispensing medicament comprising: a body; a holder, shaped to fit within the body and movable relative to the body; and receivable by said holder, a cassette containing a medicament carrier, wherein movement of the holder relative to the body results in movement of the cassette between a first position and a second position such that the cassette is reversibly removable from the holder when the cassette is in the second position.

62 Claims, 12 Drawing Sheets

MEDICAMENT DISPENSER

This application is filed pursuant to 35 USC 371 as a United States National Phase Application of International Patent Application Ser. No. PCT/EP01/12107 filed 19 Oct. 2001, which claims priority from GB 0026647.8 filed on 31 Oct. 2000 in the United Kingdom.

TECHNICAL FIELD

The present invention relates to a medicament dispenser for dispensing medicament. The invention particularly relates to an inhalation device for use in dispensing medicament.

BACKGROUND OF THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister strip containing a number of discrete doses of powdered medicament. Such devices usually contain a mechanism for accessing these doses, usually comprising either piercing means or means to peel the lid sheet away from the base sheet. The powdered medicament can then be accessed and inhaled.

It is an object of the present invention to provide a medicament dispenser (e.g. an inhalation device) which is refillable by insertion of a replacement cassette containing a medicament carrier. The cassette may be replaced when the medicament carrier is empty. The dispenser is therefore 'environmentally friendly' as the majority of the dispenser may be retained and is not disposable. It also allows the retained part of the dispenser to be fitted with additional features such as electronics which may not be cost effective on a completely disposable dispenser.

It is a further object of the present invention that the cassette may be easily removed and that a new replacement cassette can be easily inserted. It is also desirable that the operation of the medicament dispenser is straightforward and non-complex and in particular that the number of separate steps involved in preparing the dispenser for use is minimised. It is further desirable that in exceptional circumstances the cassette may be used on its own as a standalone medicament delivery system. This is especially relevant where the dispenser is designed for use in the delivery of medicament in emergency or rescue situations (e.g. asthma attacks) where simplicity and ease of use is paramount.

When not in use it is desirable from a hygiene standpoint that the dispensing part (e.g. an outlet, perhaps in the form of a mouthpiece) is provided with some kind of protective cover. The cover desirably acts both to prevent build-up of dirt on the dispensing part and to prevent ingress of dirt into the body of the dispenser through the dispensing part, which might then be subject to ingress by a patient. It is also desirable that the cover is in some way attached or mounted to the dispenser to minimise the risk that the cover is misplaced or lost. It is therefore a further object of the present invention for the body of the dispenser to act as a cover for the dispensing part when the dispenser is in storage and that the cassette is movable relative to the body to enable the dispensing part to be uncovered for use by the patient.

It is a further object of the invention to provide a medicament dispenser suitable for use with a large number of discrete doses but which is of an acceptable size for use by patients.

SUMMARY OF THE INVENTION

According to one aspect of the present invention there is provided a medicament dispenser for dispensing medicament comprising: a body; a holder, shaped to fit within said body and movable relative to the body; and receivable by said holder, a cassette containing a medicament carrier, wherein movement of the holder relative to the body results in movement of the cassette between a first position and a second position such that the cassette is reversibly removable from the holder when the cassette is in the second position.

Preferably the first position comprises a dispensing position. Preferably the second position comprises a non-dispensing position. The cassette is therefore only removable from the holder when the cassette is in the non-dispensing position.

Suitably, the cassette wholly encloses the medicament carrier and acts as a protective shell therefor.

The cassette may have any suitable form including for example, an essentially flat disc form. The holder and body may also have any suitable form. Embodiments are envisaged in which the cassette is receiving as a top-load, bottom-load or side-load.

Suitably the holder and body include attachment means to attach the holder to the body. In one aspect, said attachment means comprises a snap-fit mechanism. Suitably, the snap-fit mechanism comprises a pin and hole system.

In one aspect, the holder is pivotally movable relative to the body. In another aspect, the holder is rotationally movable relative to the body. In a further aspect, the holder is slidably movable relative to the body.

Suitably, the holder additionally comprises one or more stops to limit movement of the holder relative to the body. In one aspect, two distinct stop positions are defined corresponding to the dispensing and non-dispensing positions respectively.

Where the holder is rotationally movable relative to the body, the one or more stops suitably limit movement of the holder relative to the body to no more than about 180° rotational path. In one preferred aspect, the dispensing and non-dispensing positions are separated by about 180° rotation, and corresponding stop positions are defined.

Suitably, the one or more stops abut against the edge of the body at defined point(s) when it is moved. At these points the holder is suitably designed to click into a stop position. In aspects, in the dispensing position the stop abuts or click-engages one body edge, and in the non-dispensing position the stop abuts or click-engages another body edge.

Where the holder is rotationally movable relative to the body, the one or more stops suitably limit movement of the holder relative to the body to no more than about 180° rotational path.

Suitably, the holder additionally comprises a retainer for retaining the cassette therewithin. In one aspect, the retainer comprises a catch. The catch may for example, comprise a sprung pin which fits into a hole or an integral catch which deforms when pressed allowing removal of the cassette. Preferably, the retainer is child resistant. Child resistance may be realised by having a system which forces the user to perform two actions at once to remove the cassette. Other features of the retainer may include shock or impact resistance, the ability to lock the catch and orientation features to ensure that the cassette can only be inserted one way. The retainer should also be easy to manufacture and assemble, be robust, be composed of a minimal number of components and intrude minimally into the space into which the cassette is inserted.

Suitably, the holder includes a guide for guiding the insertion of the cassette into the holder. Preferably said guide comprise guide rails. Alternatively the guide comprises grooves, indentations or other shaping or surface details to define a 'lock and key' relationship between the holder and the cassette. Colour guides, arrows and any other surface markings may also be employed.

Suitably, the cassette additionally comprises an indexer (e.g. an indexing lever) for indexing the medicament carrier. In one aspect, the indexing lever has a finger tab located outside the body of the cassette. The rest of the indexing lever is located within the cassette. The indexing lever may have teeth at its tail end and/or teeth along its mid portion. Suitably, the indexing lever is operable (e.g. for emergency use) even when the cassette is not inserted within the holder.

Suitably, the cassette additionally comprises a dispensing outlet. The dispensing outlet may have any suitable form ranging from a simple orifice to a shaped passage (e.g. cone or tube) to a mouthpiece or nozzle. The presence of a dispensing outlet as part of the cassette itself is beneficial in that it enables the cassette to be used in emergencies as a functioning inhaler, even when the cassette is separate from its holder/body.

In aspects, the dispensing outlet is extendable. In one aspect, the dispensing outlet extends as the cassette and holder are moved from the non-dispensing position to the dispensing position.

Alternatively, the dispensing outlet is retractable (e.g. it is reversibly retractable from the cassette). In one aspect, the dispensing outlet retracts as the cassette and holder are moved from the dispensing position to the non-dispensing position.

In one aspect, the dispensing is telescopic in form. In another aspect, the dispensing outlet is fixed.

The medicament dispenser may also be designed for nasal inhalation of medicament and the dispensing outlet may therefore incorporate a nozzle ('nosepiece') as an alternative to a mouthpiece.

Suitably, the body covers the dispensing outlet and indexer when the cassette is in the non-dispensing position. This avoids the need for a separate cover and protects the mouthpiece from the ingress of dirt and contaminants during storage.

Suitably, the cassette is shaped to prevent its incorrect insertion into the holder. In one aspect, the cassette additionally comprises a raised portion to fit against the holder. The raised portion is located at the opposite end of the cassette to the mouthpiece and indexing lever and prevents the incorrect insertion of the cassette into the holder since it is too wide to fit into the holder. The raised portion is shaped such that it fits against a cut away part of the holder.

Preferably, the raised portion includes a section which is raised to define a grip portion.

The medicament carrier may have any suitable shape or form for the carrying of medicament in a variety of forms including dry powder, granule, aerosol suspension, solution including aqueous solution, capsule, nebule, pellet and tablet carrier form.

In aspects, the medicament carrier respectively comprises a capsule; a tablet carrier; an aqueous container; an aerosol container; and a dry powder container.

In one aspect, the medicament carrier comprises a container for a reservoir of dry powder. In this aspect the cassette additionally requires a meter for metering a dose of medicament. In one aspect, the dose meter defines a metering recess, wherein the metering recess communicates with the medicament container to receive a metered volume of powder when the cassette is in the non-dispensing position and the metering recess communicates with the dispensing outlet to allow passage of the metered volume of powder thereto in the dispensing position.

In another aspect, the medicament carrier comprises an elongate carrier (either linearly or angularly elongate) which may in aspects, be preloaded with medicament. The elongate carrier can take a variety of forms but preferably is a tape, web, belt, strip or cord. The powdered medicament may be retained on the carrier by electrostatic attraction, Van der Waals forces, physical attraction, mechanical binding, printing e.g. inkjet printing of the dose onto the carrier, wedging or by a cover layer or an overlying layer of the same carrier when the carrier is wound etc. One or more surfaces of the carrier and optionally the interior of the carrier may be configured to assist in retaining the particles of powder.

In one aspect, the medicament carrier comprises a blister pack, suitably in elongate form. Preferably, the medicament carrier comprises a blister strip. Preferably said blister strip comprises an elongated strip formed from a base sheet having a plurality of recesses spaced along its length and a lid sheet peelably sealed in superposed relationship thereto to define a plurality of blisters, each having therein inhalable medicament in powder form. Alternatively, the blisters may contain a tablet or an aqueous solution or suspension.

Suitably, the recesses are capsule shaped. In one aspect, the recesses are shaped for receipt by a gear or drive mechanism of the cassette. Thus, the recesses may shaped in the profile of gear teeth or in the profile of belt drive teeth. Optionally the lid sheet may contain perforations across its width spaced along the strip to allow the lid sheet to concertina when it has passed through the lid driving means. The lid sheet and/or base sheet may also optionally contain apertures or holes formed on one or both edges to fit into a sprocket.

Suitably, the cassette additionally comprises an internal mechanism for acting on the medicament carrier there within. In one aspect, the internal mechanism comprises an indexer for indexing the medicament carrier. In another aspect, the internal mechanism comprises a mover for moving the medicament carrier. In a further aspect, the internal mechanism comprises access means for accessing the medicament carrier (and hence medicament associated therewith or contained there within).

Suitably, the internal mechanism of the cassette is provided with means for engaging an externally located drive mechanism (e.g. located in the body or holder) such that it may be driven by said externally located drive.

Suitably, the body or holder additionally comprises a drive mechanism for driving at least part of the internal mechanism of the cassette. The drive mechanism is in one aspect, a manual drive (e.g. actuable by a finger or thumb movement). In another aspect, the drive may be a powered (e.g. motor) drive, as described hereinafter, which is located in the body or holder.

In one aspect, the cassette comprises an (e.g. externally protruding) indexing lever which co-operates with the internal mechanism for accessing the medicament carrier, and may be used without the body or holder if necessary in the event that mechanical or electronic breakdown of the components of the body and holder should occur, or for emergency use of the cassette as a makeshift, but functioning dispenser.

Preferably, the internal mechanism comprises:

a) an opening station for receiving a medicament carrier of the cassette, said medicament carrier having plural individual medicament containers;

b) an indexer for indexing an individual medicament container of the medicament carrier for receipt by said opening station;

c) an opener for opening said indexed individual medicament container; and d) a dispensing outlet, positioned to communicate with said opened container.

Suitably, the medicament carrier comprises a blister strip accessible by a peeling action. The peelable blister strip comprises a base sheet and lid sheet which may be peeled apart to uncover a pocket in the base sheet.

Suitably, the opener comprises peeling means positioned to engage a base sheet and a lid sheet of a peelable blister strip which has been received in said opening station for peeling apart such a base sheet and lid sheet. In one aspect, the peeling means includes lid driving means for pulling apart a lid sheet and a base sheet of a container that has been received at said opening station.

In an inhalation device aspect, the dispensing outlet is in the form of a mouthpiece through which a user can inhale to access the medicament in the opened container.

Suitably, the indexer comprises a rotatable index wheel having a recesses therein, said index wheel being engageable with a medicament carrier in use with said medicament dispenser such that said recesses each receive a respective pocket of the base sheet of a medicament carrier in use with said medicament dispenser.

Suitably, the rotatable index wheel additionally comprises a series of indentations located at its base and spaced in between the recesses.

Suitably, the indexer additionally comprises an interlock coupling to couple movement of the lever to the index wheel. The interlock coupling reversibly locks the index wheel in place. Preferably, the interlock coupling comprises a foot portion having a toe and a heel, and a tail section. Preferably, the interlock coupling is pivotally mountable to the cassette at its foot portion. Preferably, the toe fits into one of the indentations on the rotatable index wheel. Preferably, the heel is fittable into the teeth on the lever to lock the lever in place after it has been actuated by the patient. Preferably, the interlock coupling is sprung to bias it towards location of the toe in one of the indentations.

Alternatively, the indexer comprises a gear and sprocket wherein teeth on the wheel fit into apertures or holes formed on one or both edges of the blister strip. The mechanism therefore resembles that of photographic film being advanced through a camera.

Alternatively, the indexer comprises a plurality of recesses located on the tail end of the indexing lever. The recesses are shaped and sized to engage the pockets in the blister strip. Movement of the lever by the patient indexes the strip by one pocket. When the lever is then returned to its rest position the strip is disengaged and will reengage the strip one pocket further along. This indexer has the advantage that it only requires an indexing lever-additional components are not needed.

In one aspect, the indexer comprises an index ratchet which is moveable between a locked position whereby said ratchet engages a pocket on said medicament carrier and prevents further peeling thereof, and a release position allowing free movement of said medicament carrier, and actuation of said medicament dispenser actuates the lid driving means of the opener to release said index ratchet from said medicament carrier to allow peeling thereof. In this aspect, the lid driving means draws the medicament carrier through the internal accessing mechanism. The indexer stabilises and prevents further movement of the medicament carrier after the required dose of medicament has been dispensed.

Suitably, said index ratchet is pivotally mounted on said dispenser.

Suitably, the medicament dispenser further comprises an indexing lever for actuating said dispenser. Typically, said indexing lever comprises cam means for moving said index ratchet between locked and release positions, such that actuation of said lever from a stop position releases said medicament carrier for peeling thereof. Typically, said indexing lever comprises a lever ratchet for engaging said lid driving means.

Suitably, said lid driving means comprises an index gear and a drive gear which are interconnected so that the rotation of one correlates with the rotation of the other.

Alternatively, the indexer comprises an electronic drive system wherein the strip is driven by a motor. The electronic drive system additionally comprises a mechanical clamp to clamp the strip.

Suitably, said lid driving means comprises a wheel on which the lid sheet is wound up.

Typically, said lid sheet wheel has an effective winding surface, the diameter of which increases after every use of the dispenser as the lid sheet winds around the wheel.

In order to ensure that the same dose is dispensed every time, that is, only one medicament pocket is opened for every actuation of the dispenser, the dispenser may further comprise a lever stop means to limit the extent of movement of said index lever and thereby said lid driving means, in order to control the length of medicament carrier peeled by said peeling means. Hence, the medicament carrier is indexed by the same amount each time and a uniform, consistent dose is always dispensed.

The dispenser may further comprise compensating means positioned between said opening station and said lid sheet wheel for reducing the length of said lid sheet therebetween to compensate for any increase in the diameter of the effective winding surface of the lid driving means during use of the dispenser.

Typically, the compensating means takes the form of a flexible member. The flexible member may take the form of a flexible elongate arm about which the lid sheet is fed. The arm may flex inwards as tension in the lid sheet increases, and thus shorten the length of lid sheet between the opening station and the lid driving means.

Suitably, the compensating means takes the form of a spring which reduces in length as tension increase in the lid sheet between the opening station and the lid driving means. Typically a piston head is mounted on one end of the spring about which the lid sheet is fed. The other end of the spring may be fixed. As tension in the lid sheet increases the piston is driven down onto the spring.

Suitably, the compensating means takes the form of a sprung-loaded tensioner.

Suitably, the flexible member is resilient so that on removal of tension from the lid sheet, the flexible member will return to its rest position. Thus, the internal mechanism can be reloaded with a new medicament carrier after the used carrier is removed.

Alternatively, or in addition, the dispenser may comprise a clutch means to adjust for any increase in the diameter of the effective winding surface of the lid driving means during use of the dispenser. In one aspect, the clutch means communicates with the indexing means and the lid driving means, and comprises a gearing surface defining plural gear engagement positions; and plural gear teeth for engaging said plural gear engagement positions, wherein the plural gear teeth are arranged such that at any one time only a single gear tooth engages a single gear engagement position.

It will be appreciated that, in use, the clutch means acts to compensate for the increase in diameter of said effective winding surface of the lid driving means. The clutch means allows for slippage when the tension in the lid sheet is greater than the force required to peel apart the lid sheet and the base sheet.

It will be appreciated that in total, the clutch means effectively defines a number of individual gear positions which is greater than the number of gear engagement positions. This is therefore advantageous over a traditional slipping clutch arrangement comprising intermeshing gear wheels, where the effective number of individual gear positions defined is either equal to, or no more than, the number of gear engagement positions defined by one of the gear wheels. The clutch means herein is also typically more compact than traditional slipping clutch arrangements e.g. because it enables smaller gearing surfaces to be employed.

In a preferred aspect, the gearing surface and plural gear teeth are arranged such that the number of individual gear positions defined is equal to the number of gear engagement positions multiplied by the number of gear teeth. In one example, if the gearing surface defines 60 gear engagement positions and there are 6 gear teeth, then up to 360 individual gear positions are definable (e.g. 1° resolution on a rotating gear system).

Suitably, the gearing surface defines from 20 to 100, preferably from 40 to 80 gear engagement positions. Suitably, the number of gear teeth is from 2 to 20, preferably from 3 to 10.

In one aspect, the gear engagement positions are equally spaced (e.g. equidistantly spaced) and the gear teeth are offset (e.g: non-equidistantly spaced) relative thereto. Such offset arrangement maximises the number of effective individual gear positions which are capable of definition. An example of this aspect, is a Vernier spring arrangement.

In another aspect, the gear engagement positions are also equally spaced (e.g. equidistantly spaced) and the gear teeth are located on a wobbling element capable of wobbling the gear teeth to plural offset (e.g. non-equidistantly spaced) positions. Such a wobbling offset arrangement also maximises the number of effective individual gear positions which are capable of being defined. An example of this aspect, is the wobbling wheel arrangement described herein.

In aspects, the clutch means is non-integral with either of the lid driving means or the indexing means, but forms a separate interconnecting component.

Suitably, the gearing surface comprises a gear wheel. As used herein, the term gear wheel encompasses, for example, a wheel, spindle or spool.

Suitably, the gear teeth may be arranged to be in ratchet form (i.e. enabling movement in one direction only).

Suitably, the gearing surface and gear teeth are in biased (e.g. sprung) engagement.

In one aspect, the lid driving means comprise a wheel on which the lid sheet is wound up. Suitably, said wheel has a winding surface which decreases in diameter when tension in the lid sheet increases. Suitably, the wheel comprises a plurality of resiliently flexible arms each extending therefrom at an angle with respect to a radius. The leading end of the lid sheet is looped over one of said resiliently flexible arms to secure the lid sheet to the wheel initially.

In another aspect, the lid driving means comprise a mangle. The lid sheet passes through two rotating wheels which act as a mangle and is gripped at the point of contact with the wheels. The used portion of the lid sheet is collected in a chamber after it has passed through the mangle.

In another aspect, the lid driving means comprise a roller. Suitably, the roller is composed of a polymeric rubber and is positioned next to a guide wall. Suitably, the roller has a smooth surface. Alternatively, the roller has a knurled surface. The roller grips the lid sheet as it passes from the point at which it is separated from the base sheet through the space between the roller and the guide wall and the used portion of the lid sheet is then collected in a chamber. The roller has the advantage over the mangle described above in that a greater degree of contact between the roller wheel and the lid sheet occurs—the lid sheet is squeezed through the roller and may pass around about ⅓ of the roller wheel. This provides a higher level of grip and pulling force than with a mangle. The force required to turn the roller is constant throughout the use of the device and does not vary according to how much of the lid sheet has been peeled away from the base sheet. This is in contrast to the wheel described above where the forces required to turn the wheel may vary due to the fact that the lid sheet is wound around the wheel. The lid sheet is not wound around the roller. The roller also has the advantage that the lid sheet does not have to be looped around or fixed to the roller before use of the device, therefore simplifying assembly of the device and reducing costs.

In a further aspect, the lid driving means comprise a lid spool. The lid spool comprises a toothed wheel with a central upward cylindrical projection on which the lid sheet may be wound when it has been separated from the base sheet. The lid spool has teeth around its base which fit into teeth on the lever. The lid spool is therefore driven by the movement of the indexing lever and the lid sheet is pulled away from the base sheet and wound onto the lid spool, causing the rotatable indexing wheel to turn and index the base strip by one dose. The interlock coupling, as described above, is moved along the base of the rotatable indexing wheel until it fits into the next base recess. The positioning of the interlock coupling in this recess limits the movement of the lid spool to the distance between two pockets on the base sheet and therefore prevents the amount of lid sheet which is wound around the lid spool from increasing as the diameter of the lid spool is increased.

In a further aspect, the lid driving means comprise a spiked wheel. As the spiked wheel turns, the lid sheet is pulled over it and the spikes perforate parts of the lid sheet to improve the grip on the lid sheet. The lid sheet then passes out into a chamber where it collects.

In a further aspect, the lid driving means comprise a clamp system. The clamp system comprises at least one angled spring which is pivotable at one end and grips the lid sheet at the other end. The clamp system is moved in the direction that the lid sheet is to be pulled and grips the lid sheet, pulling it and therefore peeling it away from the base sheet. The clamp system is then moved back to its rest position. This results in the spring pivoting and clamping the lid sheet, therefore preventing the lid sheet from being further peeled from the base sheet.

Suitably, the lid driving means is operable by an electronic drive system. The electronic drive system may also be used in conjunction with a mechanical drive system.

Suitably, the electronic drive system is located in either the body or the holder part and the cassette comprises the minimum number of component (i.e. internal mechanism) parts. In embodiments, the body/holder including the electronic drive system is designed to be retained by the user and the cassette is sold as a refill/reload component which is discarded after use. By locating the electronic drive system in the body/holder, the amount of electronic components which are discarded is minimised.

The electronic drive system typically comprises a motor, preferably an electrically-powered motor. The motor may provide linear or rotary drive, but in general, rotary motors are most suitable. The motor may for example, comprise a DC electric motor, a piezoelectric (PZ) motor, an ultrasonic motor, a solenoid motor or a linear motor. Preferably, the electronic drive system comprises a DC motor, a PZ motor or an ultrasonic motor.

The use of ultrasonic motors is particularly preferred since they offer advantages over conventional motors in terms of weight, size, noise, cost and torque generated. Ultrasonic motors are well known in the art and are commercially available (e.g. BMSTU Technological Cooperation Centre Ltd, Moscow, Russia; Shinsei Corporation, Tokyo, Japan).

Ultrasonic motors do not use coils or magnets but comprise a piezo-electric ceramic stator which drives a coupled rotor. The stator generates ultrasonic vibrations which in turn causes rotation of the rotor. While regular DC motors are characterised by high speed and low torque, requiring reduction gearing to increase torque, ultrasonic motors attain low speed and high torque, thus eliminating the need for reduction gearing. Furthermore, these motors are lightweight and compact, lacking coils and magnets, and are noiseless as the ultrasonic frequencies used are not audible to the human ear.

Suitably, the dispenser further comprises actuating means for actuating said electronic drive system. Said actuating means may take the form of a switch, push-button, or lever.

In another aspect, the used portion of the lid sheet may be passed around rollers and fed back onto the used portion of the base sheet after the medicament has been accessed to join back onto the base sheet. The lid sheet may be coated with a sticky substance to aid resealing. The use of this mechanism saves space as the used portions of the blister strip will be collected in the same area.

In a further aspect, the coil comprising the unused blister strip may be surrounded by a constant force spring. Alternatively the coil comprising the unused blister strip may be surrounded by an elastomeric band or band comprising a contractible material. The constant force spring, elastomeric band or band comprising a contractible material contracts as the coil reduces in size.

Suitably, the peeling means additionally comprise a guide for guiding the lid sheet and base sheet along separate paths at the opening station. The lid sheet is passed around the guide portion onto the lid driving means.

Suitably, the guide comprises a structure fixed in position in the cassette.

Alternatively, the guide comprises a roller mechanism. The lid sheet is fed over the rollers onto the lid driving means.

Suitably, the cassette comprises a first chamber for holding the medicament carrier when charged with medicament and a second chamber to receive the medicament carrier after release of medicament therefrom. Where the medicament carrier is in multi-dose form, it may feed from the first chamber into the second chamber by way of the opening (or access) station. Thus, in use that part of the medicament carrier which is charged with medicament is held in the first chamber and that part which is empty (i.e. from which medicament has been discharged or otherwise released) is in the second chamber. In one aspect, the first chamber initially houses a charged elongate blister strip and the second chamber receives the used portion of the base sheet after it has been indexed around the index wheel and separated from the lid sheet.

Suitably, the first chamber and second chamber are separated by a wall.

Suitably, the wall is movable to adjust the size of the first and second chambers.

Suitably, the wall is pivotally mountable e.g. the wall is mountable on a pin fixed into the cassette. Alternatively, the wall is slidably mountable.

Suitably, the wall additionally comprises at least one brush located along its top or bottom side which brush against the top and bottom surfaces of the inside of the cassette. The brushes may act to close off the chamber from the rest of the body of the cassette and to prevent any loose powder from entering the rest of the cassette. Loose powder may enter the chambers from the used portion of the blister strip if the patient indexes the strip by pressing the lever when they do not intend to take a dose or when they fail to inhale all the powder.

Alternatively, the wall additionally comprises at least one flexible seal portion located along its top-or bottom side. The seal may act in the same way as the brushes described above and seal off the chamber from the rest of the body.

Alternatively, the wall is flexibly movable to adjust the size of the first and second chambers.

Alternatively, the second chamber is expandable to create space for the growing coil of the used portion of the base sheet.

Suitably, the cassette further comprises a third chamber to receive the used portion of the lid sheet and a fourth chamber which houses the index wheel. The fourth chamber communicates via a slit, which in turn extends upwardly within a dispensing outlet and communicates with air inlets.

Suitably the internal mechanism additionally comprises a crushing wheel to crush the blister pockets after the medicament has been removed from them. The crushing wheel therefore reduces the space, which the used portion of the base sheet takes up.

Suitably, at least a portion of the holder and body are shaped for ease of grip by the user. Suitably, operation of the medicament dispenser may be performed with one hand.

Suitably, the medicament dispenser comprises an actuation or dose counter for counting the number of actuations of the indexing lever or releases of dose from the cassette. The dose counter may count the number of doses left to be taken or the number of doses taken. Suitably, the dose counter is electronic or mechanical.

In one aspect, the dose counter is located within the cassette. Alternatively, the dose counter is external to the cassette.

In one aspect, the medicament carrier (e.g. a blister strip) has printed numbers on it corresponding to the doses in the pockets. Suitably, the printed numbers are visible through a window in the cassette.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system is arranged to be responsive to or activated by the voice of a user. Thus, for example the system may be switched on or off in response to a voice command.

The electronic data management system may be integral with the body. Alternatively, the electronic data management system forms part of a base unit which is reversibly associable with the body.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Energy may be conserved by a variety of means to enable the device to operate for longer on a given source of energy, such as a battery. Energy conservation or saving methods have additional advantages in terms of reducing the size requirements of the power source (e.g. battery) and thus the weight and portability of the medicament dispenser.

A variety of energy saving methods is available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Suitably, the system additionally comprises a visual display unit for display of data from the electronic data management system to the user. The display may for example, comprise a screen such as an LED or LCD screen. More preferably the visual display unit is associable with the body of the medicament dispenser.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement cassettes. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hard-wired link, an infra red link or any other suitable wireless communications link.

Suitably, the medicament dispenser additionally comprises an actuation detector for detecting actuation of the dispensing mechanism wherein said actuation detector transmits actuation data to the electronic data management system.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the release means. The time delay is typically of the order of from three to thirty seconds.

Suitably, the medicament dispenser additionally comprises a release detector for detecting release of medicament from the cassette, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the medicament dispenser additionally comprises a breath trigger for triggering the dispensing mechanism, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analysed waveform.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser comprises in association with a body or holder thereof, a first transceiver for transmitting and receiving data and in association with the medicament carrier, a second transceiver for transmitting and receiving data, wherein data is transferable in two-way fashion from the first transceiver to the second transceiver. The data is preferably in digital form and suitable for transfer by electronic or optical means. A medicament dispenser of this general type is described in pending UK Patent Application No. 0020538.5.

One advantage of embodiments of this type is the ability to store many types of information in different parts of the memory structure of the transceivers. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

On loading or reloading the medicament dispenser with a cassette the second transceiver may, for example, read the unique serial number, batch code and expiry date of the medicament and any other information on the second transceiver. In this way the nature and concentration of the medicament, together with the number of doses used or remaining within the cassette, may be determined. This information can be displayed to the patient on a visual display unit. Other information, such as the number of times the medicament dispenser has been reloaded with a cassette, may also be displayed.

Similarly, should the cassette be removed from the holder before the supply of medicament is exhausted, the same data can be read from the second transceiver and the number of doses remaining or used determined. Other information, such as the date and time of administration of the drug, or environmental exposure data such as the minimum/maximum temperatures or levels of humidity the cassette has been exposed to, may also be read and displayed to the user.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the device. Or alternatively, data may be stored in a database memory of the electronic data management system and periodically downloaded to any transceiver. In either case, a history of the usage of the device may be built up in the memory of a transceiver.

In one embodiment herein, a history of the usage of the medicament dispenser is transferred to the second transceiver. When the blister strip in the cassette is exhausted it is exchanged by the patient for a new refill cassette. At the point of exchange, which will typically occur at the pharmacy, data may be transferred from the exhausted cassette to the refill and vice-versa. Additionally, usage history data may be read from the refill and transferred to a healthcare data management system for example comprising a network computer system under the control of a healthcare data manager.

Methods are envisaged herein whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or one dispensing) to or from any transceiver can be arranged to be readily achievable by the use of a reader which is remote from the medicament dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly-powered and the term passive is used to mean indirectly-powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver. Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or holder of the medicament dispenser or on the cassette.

In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is mouldable or weldable to the cassette or housing. Suitably, the carrier encases the tag. More preferably, the carrier forms a hermetic seal for the tag.

In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system. Dispensers employing such communicators are described in pending PCT Applications No.s PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto. More preferably, information from the user-specific network address can be made available to the remote information source.

In one aspect, the remote information source is a medicament prescriber, for example a doctors practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests which have been remotely pre-authorised by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

Suitably, the medicament dispenser additionally comprises a geographic positioning system such as a global positioning system or a system which relies on the use of multiple communications signals and a triangulation algorithm.

Suitably, the medicament carrier has medicament associated therewith. Suitably, the medicament is selected from the group consisting of albuterol, salmeterol, fluticasone propionate and beclomethasone dipropionate and salts or solvates thereof and any combination thereof. Preferably said combination comprises salmeterol xinafoate and fluticasone propionate.

Suitably, the medicament additionally comprises an excipient. Preferably said excipient is a sugar.

According to another aspect of the present invention there is provided the medicament dispenser described above in kit of parts form. A first part of the kit comprises a body; a holder, shaped to fit within said body and movable relative to said body; and within said holder a receiving station for receipt of a cassette. A second part of the kit comprises a cassette containing a medicament carrier, wherein the cassette is receivable by the receiving station and movement of the holder relative to the body results in movement of the cassette between a first position and a second position such that the cassette is reversibly removable from the receiving station when the cassette is in the second position.

Suitably, the cassette includes an internal mechanism for acting on said medicament carrier, and the body or holder comprises a drive mechanism for driving said internal mechanism of the cassette. In aspects, the internal mechanism comprises an indexer for indexing the medicament carrier; a mover for moving the medicament carrier; and/or access means for accessing the medicament carrier.

Suitably, the body or holder additionally comprises a drive mechanism for driving at least part of the internal mechanism of the cassette. In aspects, the drive mechanism is a manual or powered drive mechanism.

In one aspect, the medicament dispenser may be assembled as follows. The holder is snap fitted into the body. The cassette is assembled separately. The body of the cassette is formed, preferably in two sections with any necessary spindles or integral components formed into the base. Individual components such as indexing wheels, lid winding mechanisms, guide portions etc are then assembled into the base. Finally the medicament carrier (e.g. an elongate blister pack) is inserted into the cassette. This may be wound into the dispenser before the lid is attached to the cassette and the cassette sealed. Alternatively, the cassette may be formed completely apart from a hole left in its side for insertion of the medicament carrier. The hole may then be sealed to complete the cassette. This second method of inserting the medicament carrier into the device has the advantage that it is much simpler.

BRIEF DESCRIPTION OF THE DRAWINGS

The invention will now be further described by reference to the accompanying drawings in which:

FIGS. 9b and 9c show respective side views of the holder/body and cassette of the medicament dispenser of FIG. 9a;

DETAILED DESCRIPTION OF THE DRAWINGS

Figure 1:
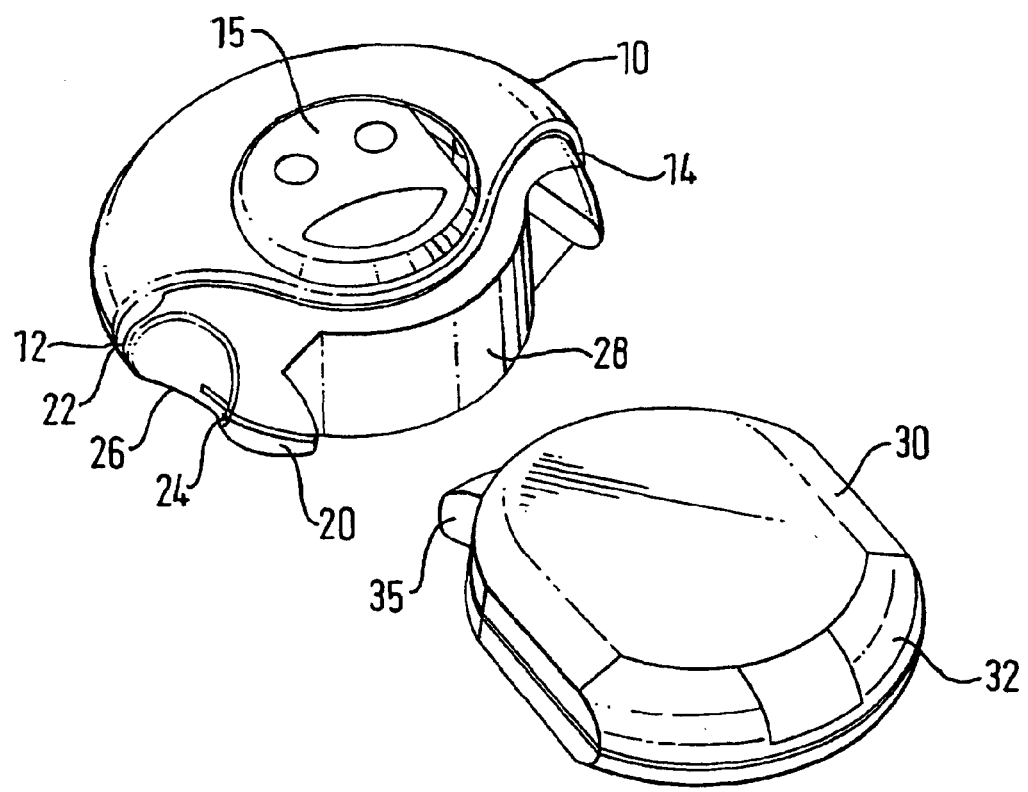
FIG. 1 shows a perspective view of a medicament dispenser according to the invention with the cassette removed from the holder and body.

FIG. 1 shows a medicament dispenser in accord with the present invention, comprising a body 10, a holder 20, refill cassette 30 and electronic display 15. The holder 20 is shaped to fit snugly inside body 10 and is fixed to a point on the body (not shown) about which it rotates. Stops 22, 24 protrude from the holder 20 and prevent the holder 20 from rotating more than about 180° relative to the body 10. The stops 22, 24 also provide two defined positions of the holder 20 within the body 10. One position is defined by stop 22 meeting with body edge 12 and the other position defined by stop 24 meeting with body edge 14 when the holder has been rotated relative to the body. The area between stops 22 and 24 is shaped to form a thumb or finger grip 26 for the user of the device. The holder 20 forms a shell into which the refill cassette 30 snugly fits.

The refill cassette 30 comprises a shell containing the medicament carrier (not shown) and a mechanism for opening the carrier (not shown) for the medicament to be accessed. The refill cassette 30 has a raised portion 32 at one end on both sides along its width so that this part of the refill cassette 30 is at least the same depth as the part of the holder 28 which receives the refill cassette 30. This allows the position of the cassette 30 within the holder 20 to be fixed such that the ridge 32 protrudes from the holder 20 but the rest of the cassette 30 is contained within the holder 20.

The refill cassette 30 also has a mouthpiece (not shown) and an indexing lever 35 for indexing the medicament carrier within the cassette 30.

Figure 2:
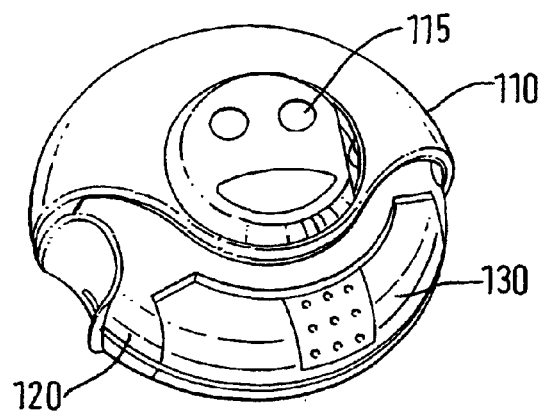
FIG. 2 shows a perspective view of the medicament dispenser of FIG. 1 with the cassette inserted into the holder and body in the non-dispensing position.

FIG. 2 shows the medicament dispenser according to the present invention with the cassette 130 in place in the holder 120 and body 110 in the non-dispensing position. The cassette 130 is fixed in place by a catch (not shown). The catch can be made to be child resistant to prevent children from removing the cassette 130 from the holder 110. When the cassette 130 is in the position shown, relative to the holder 120, the body 110 covers the mouthpiece (not shown) and a separate mouthpiece cover is therefore not required. The body 110 also protects the indexing lever (not shown) and this prevents accidental indexing of the medicament carrier (not shown) when the medicament dispenser is not in use.

Figure 3A:
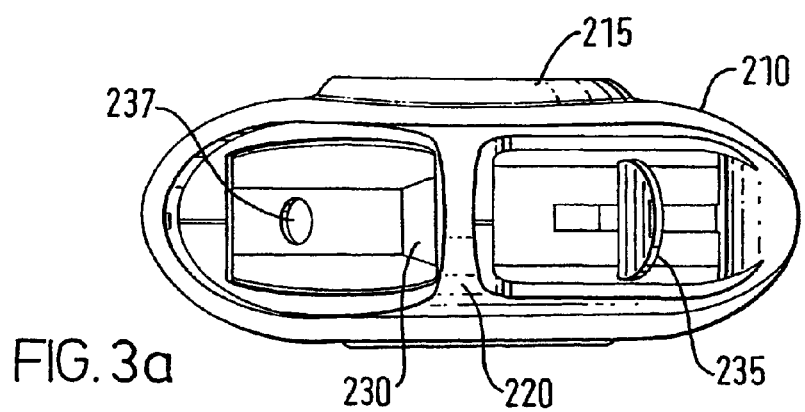
FIGS. 3a and 3b show perspective views of the medicament dispenser of FIGS. 1 and 2 with the cassette in the dispensing position.
Figure 3B:
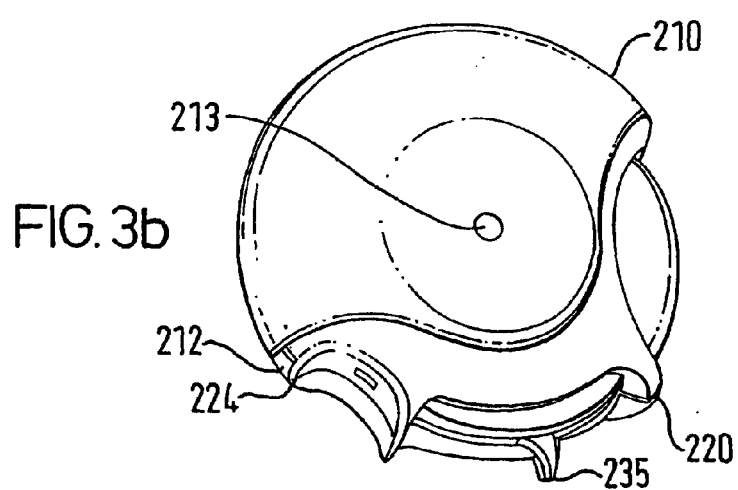

FIGS. 3a and 3b show the medicament dispenser of FIGS. 1 and 2 with the cassette 230 in place in the holder 220 in the dispensing position. The holder 220 has been rotated relative to the body 210 so that stop 224 abuts body edge 212. It can be seen that the holder 220 has cut away portions on its depth to allow access to the indexing lever 235 and the mouthpiece 237. FIG. 3*b* also shows the attachment point 213 at which the holder 220 is attached to the body 210.

Figure 4:
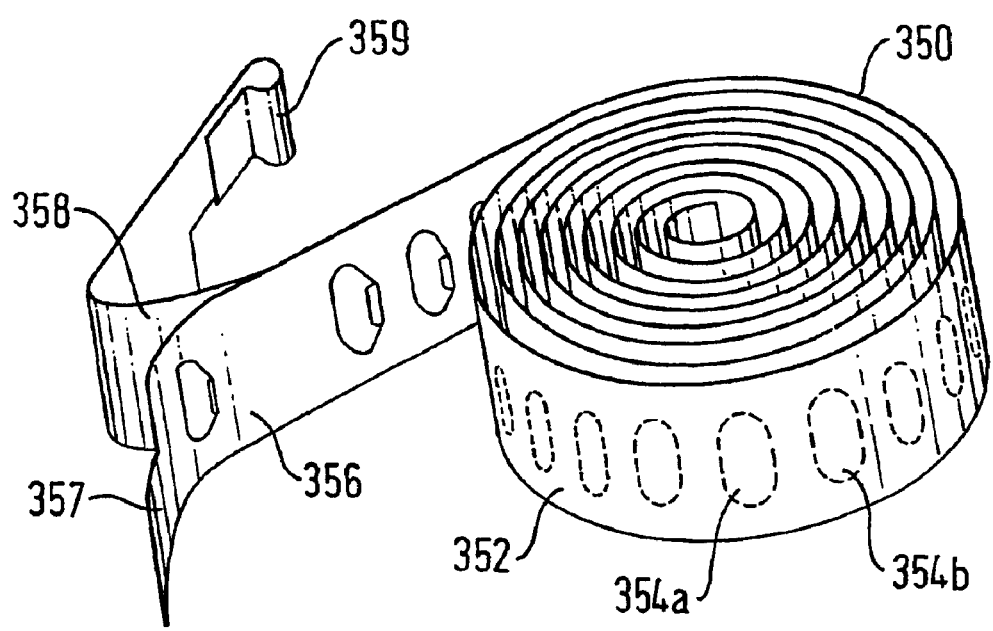
FIG. 4 shows a perspective view of a medicament carrier for use in accord with the present invention.

FIG. 4 shows a medicament carrier 350 for use herein. The medicament carrier comprises a peelable blister strip 352 defining a plurality of pockets 354*a*, 354*b* each of which contains a dose of medicament which can be inhaled, in the form of powder.

The strip comprises a base sheet 356 in which blisters are formed to define the pockets 354*a*, 354*b* and a lid sheet 358 which is hermetically sealed to the base sheet except in the region of the blisters in such a manner that the lid sheet 358 and the base sheet 356 can be peeled apart. The sheets 356, 358 are sealed to one another over their whole width except for the leading end portions 357, 359 where they are preferably not sealed to one another at all. The lid 358 and base 356 sheets are each preferably formed of a plastics/aluminium laminate and are preferably adhered to one another by heat sealing.

The strip 352 is shown as having elongate pockets 354*a*, 354*b* which run transversely with respect to the length of the strip 352. This is convenient in that it enables a large number of pockets 354*a*, 354*b* to be provided in a given strip 352 length. The strip 352 may, for example, be provided with sixty or one hundred pockets 354*a*, 354*b* but it will be understood that the strip 352 may have any suitable number of pockets 354*a*, 354*b*.

Figure 5A:
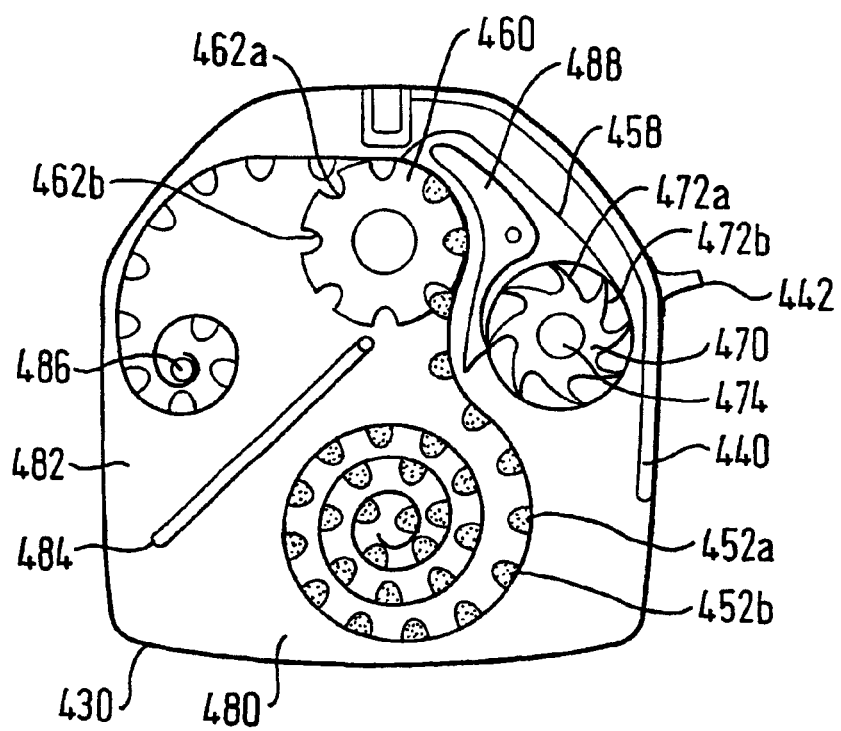
FIG. 5a shows a sectional view of an internal mechanism of a cassette in accord with the present invention with the majority of the medicament carrier unused.
Figure 5B:
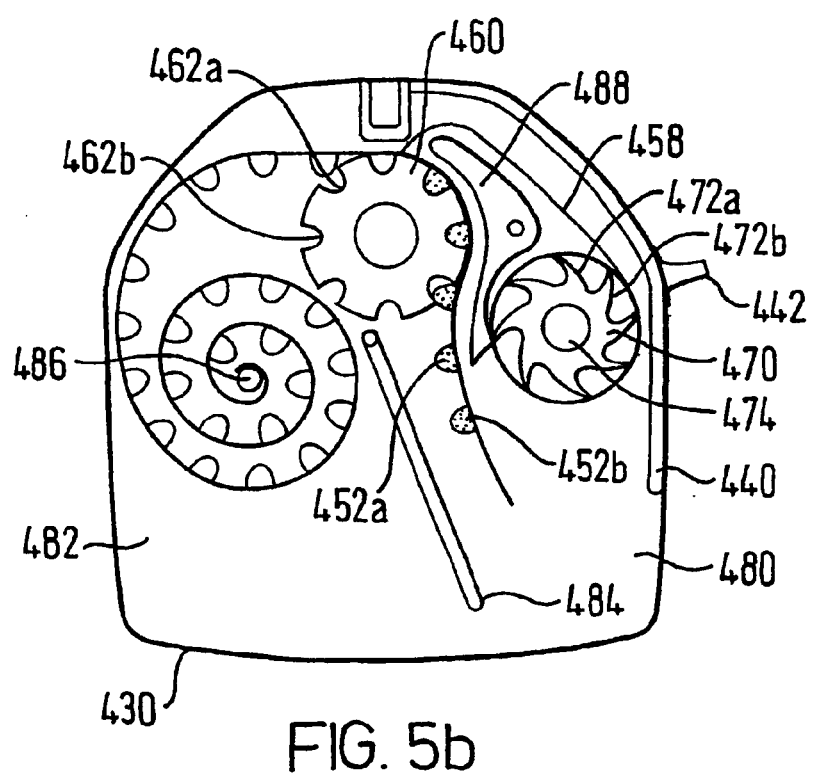
FIG. 5b shows a sectional view of the internal mechanism of the cassette of FIG. 5a with the majority of the pockets of the medicament carrier empty.

FIGS. 5*a* and 5*b* show an internal mechanism of a cassette 430 containing a medicament carrier 450. FIG. 5*a* shows the medicament carrier 450 in the situation where the majority of the pockets 454 are still filled with powder. FIG. 5*b* shows the situation where the majority of pockets 454 are empty and most of the lid sheet 458 has been removed from the base sheet 456.

The internal mechanism comprises an index wheel 460 and a lid-winding wheel 470 for winding the used portion of the lid sheet 458. The index wheel 460 has a plurality of recesses 462*a*, 462*b* extending parallel with the axis of the wheel.

The recesses 462*a*, 462*b* are spaced at a pitch which is equal to the distance between the centre lines of adjacent pockets 452*a*, 452*b*.

The mechanism of the cassette 430 further comprises a lever 435, which comprises an arcuate wall with a finger tab 437 protruding from the cassette 430 and an arm that extends inwardly from the wall.

The cassette 430 also includes an area 480 for the medicament carrier 450 to be coiled in prior to use of the doses contained inside it and an area 482 where the used base of the medicament carrier 450 is collected. Area 482 contains base winding wheel 490 on which the used portion of the base sheet is wound. Also included is a movable wall 485 to separate these two areas to form two chambers 480, 482. The movable wall 485 is pushed from the position shown in FIG. 5*a* by the growing coil of collected base sheet to the position shown in FIG. 5*b*, thereby adjusting the size of the chambers.

The lid winding wheel shown in FIGS. 5*a* and 5*b* takes the form of a collapsible wheel 470. The collapsible wheel 470 has a series of resilient arms 472*a*, 472*b* radiating from a central shaft 474, each at an angle to a radius. The leading end of the lid sheet 458 is looped over one of these resilient arms 472*a* and the lid sheet 458 is wound onto the collapsible wheel 470 as it is peeled away from the base sheet 456. As more lid sheet 458 is wound onto the collapsible wheel 470, the resilient arms 470*a*, 470*b* gradually flex inwardly, and the effect is to keep the external diameter of the reel of wound up lid sheet 458 substantially constant while the internal diameter decreases. Guide portion 490 guides the lid sheet from the point at which it is separated from the base sheet to the lid winding wheel.

Figure 6:
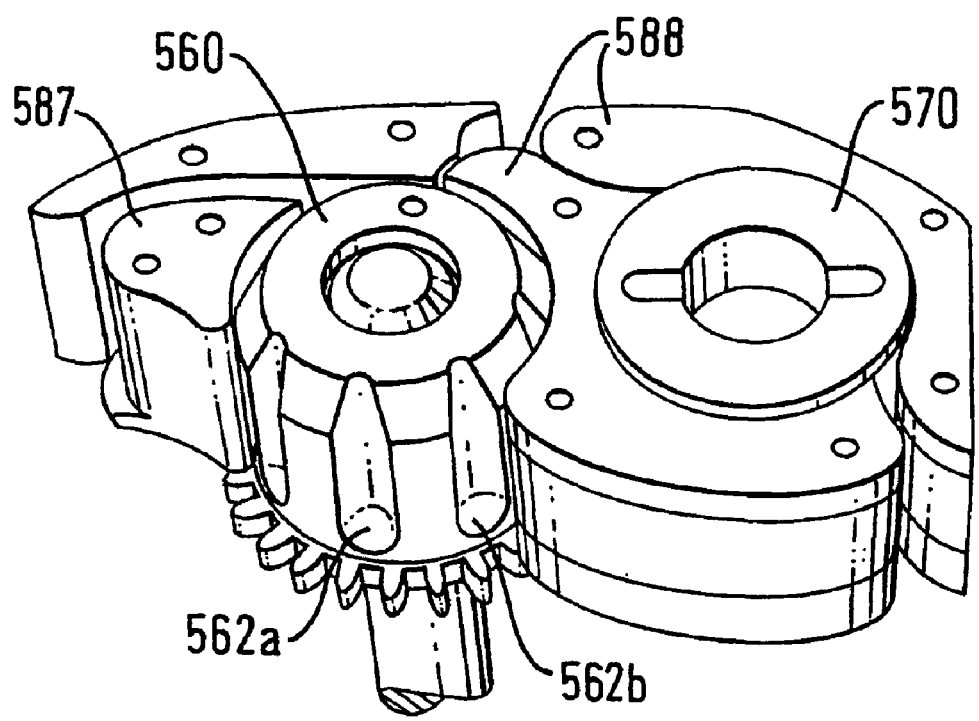
FIG. 6 shows a perspective view of a second internal mechanism in accord with the present invention.

FIG. 6 shows an alternative internal mechanism of the cassette which substitutes for that shown in FIGS. 5*a* and 5*b*. The mechanism is shown without the medicament carrier in place, without the base winding wheel, chambers for housing the medicament carrier or the movable wall to separate the chambers. The lever is also not shown.

The mechanism comprises index wheel 560 and lid winding roller 570. The index wheel 560 has a plurality of recesses 562*a*, 562*b* spaced at a pitch equal to the distance between the centre lines of adjacent pockets 552*a*, 552*b* in the medicament carrier. The mechanism also comprises guide portions 590 and 595 which guide the lid and base sheets (not shown) away from each other and toward the base winding wheel (not shown) or lid winding roller 570 as appropriate. The used portion of the lid sheet is gripped tightly by the roller 570 as it passes through from the guide portion 590 and is then passed out into the rest of the cassette to collect in a chamber. Use of the roller 570 has the advantage over the collapsing wheel in that the leading end of the lid sheet does not need to be tied on but is merely gripped by the roller 570, therefore simplifying the assembly process.

In operation, the user moves the holder relative to the body to move the cassette into the dispensing position and then presses on the finger tab of the lever to cause it to move. This leads to rotation of the index wheel which results in rotation of both the base winding wheel and the lid winding wheel, thus peeling the base sheet and lid sheet apart over a distance sufficient to expose a previously unopened pocket opposite the end of the powder outlet. The patient can then inhale the powdered medicament through the mouthpiece.

Figure 7A:
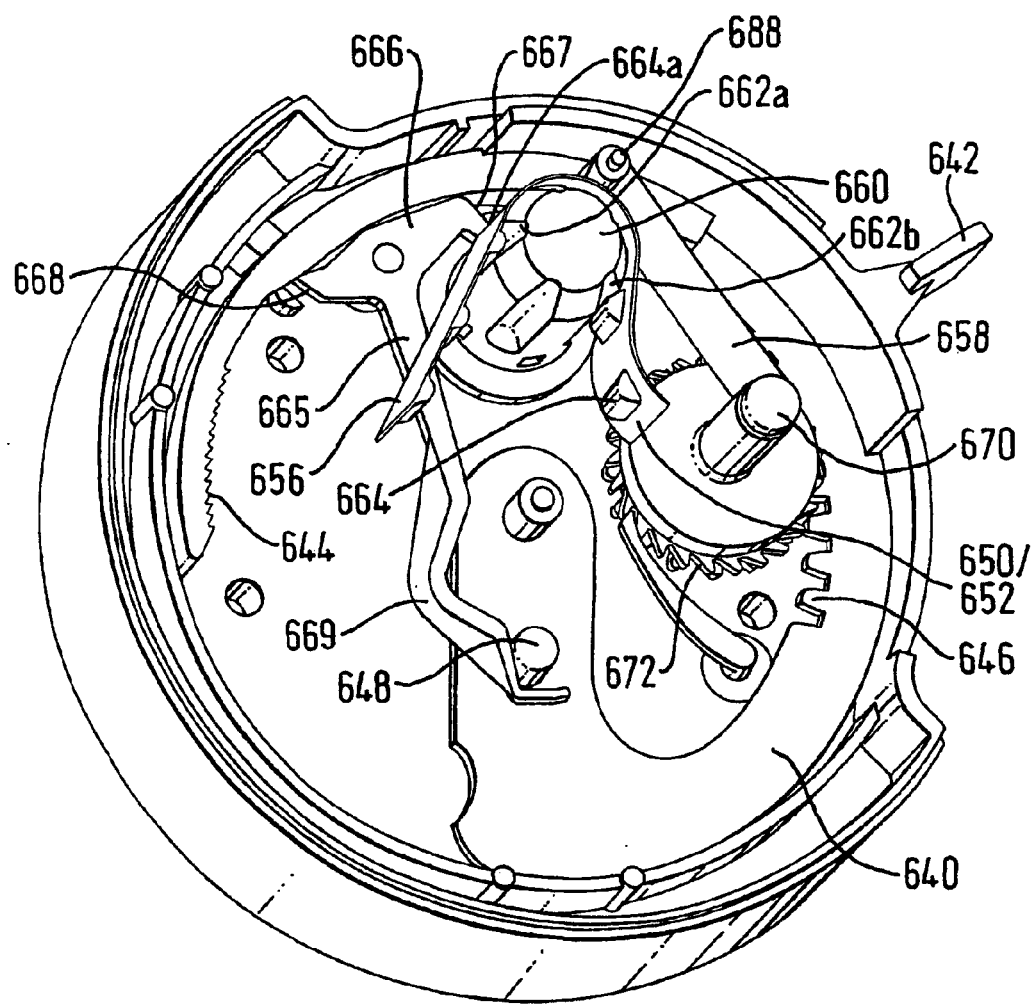
FIGS. 7a shows a perspective view of a third internal mechanism in accord with the present invention when the lever has not been actuated.
Figure 7B:
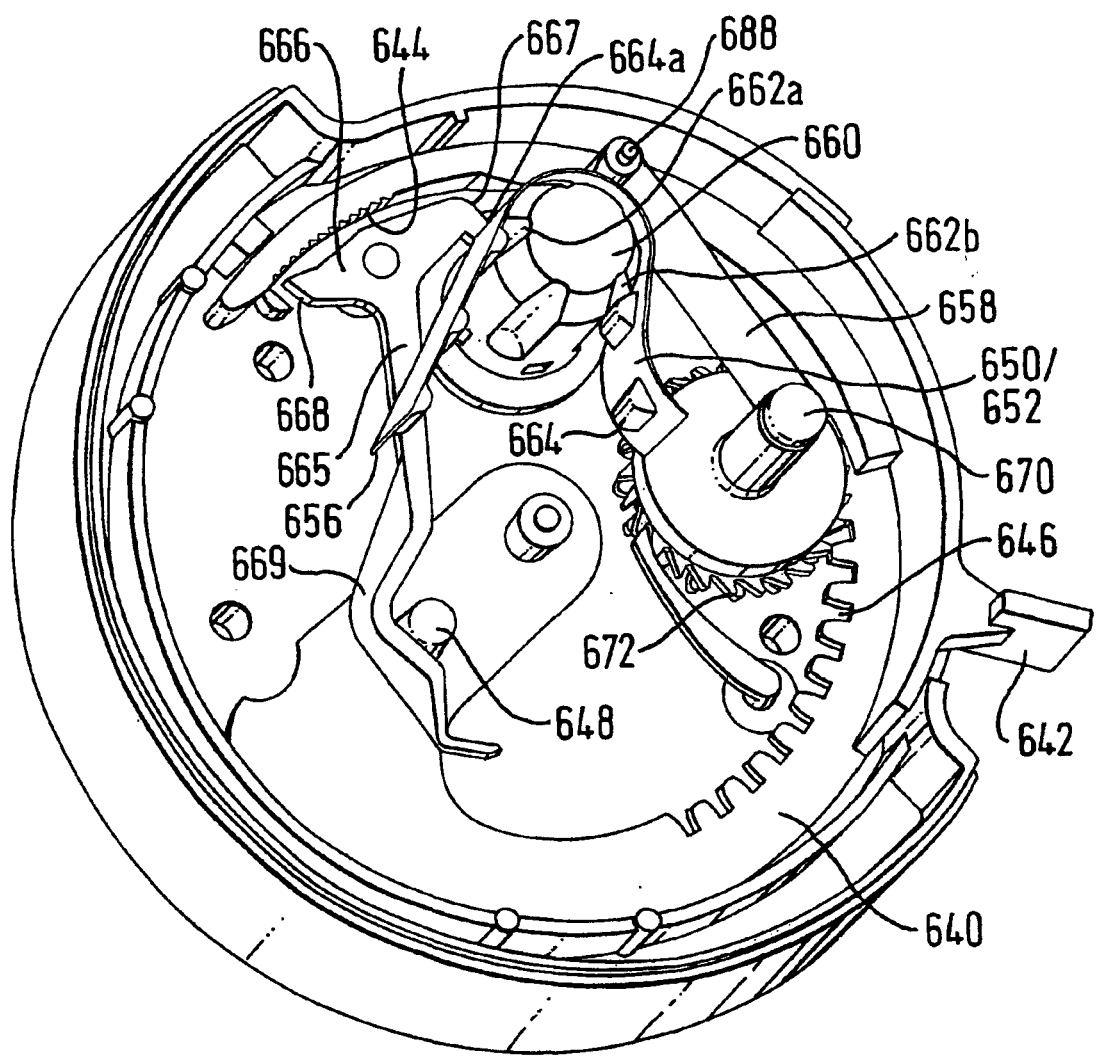
FIG. 7b shows a perspective view of the internal mechanism of FIG. 7a when the lever has been fully actuated.

A further alternative internal mechanism is shown in FIGS. 7*a* and 7*b*. The mechanism comprises an index wheel 660 and a lid spool 670. The lid spool 670 comprises a toothed wheel 672 with a central upward cylindrical projection on which the lid sheet 658 is wound when it has been separated from the base sheet. The index wheel 660 is similar to that shown in FIGS. 5 and 6 and has a plurality of recesses 662*a*, 662*b* spaced at a pitch equal to the distance between the centre lines of adjacent pockets 664 in the medicament carrier 650. The index wheel 660 however, additionally has a plurality of indentations 664*a*, 664*b* which are spaced at intervals in between the recesses 662*a*, 662*b*. The teeth 672 on the base of the lid spool fit into the teeth 646 on the indexing lever 640 on its mid portion. The lid spool 670 is driven by movement of the index lever 640 and its interaction with the teeth 646 on this lever 640.

As more lid sheet 658 is wound around the lid spool 670 its diameter increases therefore a mechanism is required to ensure that the medicament carrier 650 is indexed by the same amount each time. Interlock coupling 665 comprises a foot portion 666 having a toe 667 and a heel 668, and a tail section 669. The interlock coupling 665 is pivotally mountable to the cassette at its foot portion 666. The toe 667 of the interlock coupling 665 is shaped to fit in an indentation 664 on the index wheel 660 and the heel 668 is able to communicate with the teeth on the tail section 644 of the indexing lever 640. The interlock coupling 665 is sprung biased towards the index wheel 660. A ratchet pawl is provided on the lid spool 670 to stop the used portion of the lid sheet 658 from unwinding from the lid spool 670 and to ensure that the tension in the wound lid sheet 658 is maintained.

FIG. 7a shows the mechanism when the index lever 640 has been marginally moved from its rest position. It can be seen that the toe 667 of the interlock coupling 665 has just been moved out of an indent 664 in the index wheel 660. The heel 668 of the interlock coupling 665 is in contact with the indexing lever 640. The tail section 669 of the interlock coupling 665 is in contact with a projection 646 from the index lever 640. The unused portion of the blister strip 652 is fed onto the index wheel 660 and the lid sheet 658 is then separated from the base sheet 656 and passes around a roller guide 688 before being wound around the lid spool 670.

As the indexing lever 640 is moved by the patient, the lid spool 670 is turned by interaction with the teeth on the lever 640, resulting in the lid sheet 658 being peeled away from the base sheet 656 and wound around the lid spool 670. The index wheel 660 is turned as the lid sheet 658 is peeled away until the toe 667 of the interlock coupling inserts into the next indentation 664. The heel 668 of the interlock coupling 665 moves against the tail end of the indexing lever 640 and interacts with the teeth 644 on this part of the indexing lever 640. The tail section 669 of the interlock coupling 665 is swung around the projection 648 on the lever 640 so that the projection 648 gradually travels along the tail section 669 of the interlock coupling 665 towards its middle.

The positioning of the mechanism when the index lever 640 has been fully moved is shown in FIG. 7b. The toe 667 of the interlock coupling 665 has been inserted into the next indentation 664 and the heel 668 has fitted into the teeth 644 at the tail end of the indexing lever 640 to lock the lever 640 in place so that it can not be moved any further. The next pocket 654 on the blister strip 650 is aligned with the mouthpiece (not shown) and air inlet (not shown) ready for inhalation by the patient.

Figure 8:
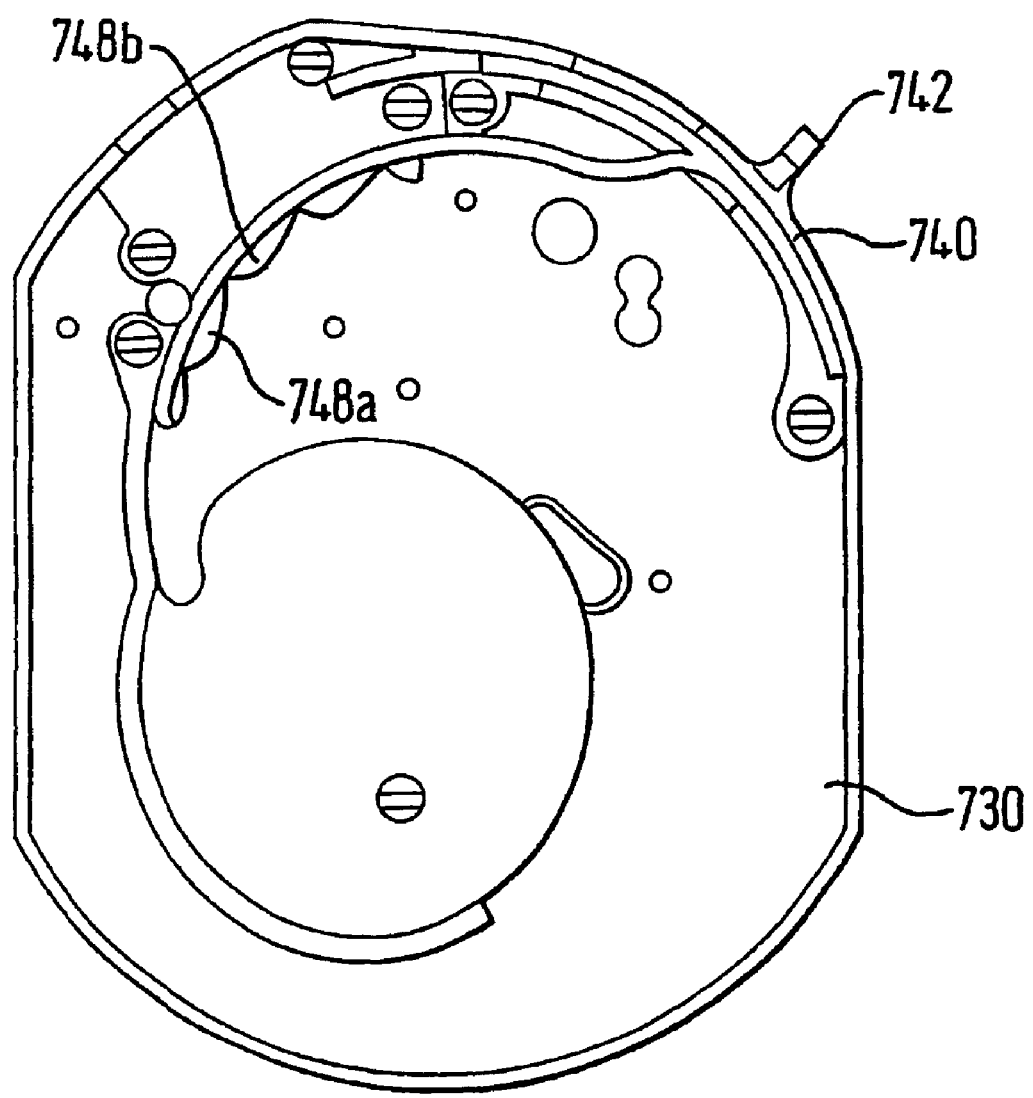
FIG. 8 shows a sectional view of an indexing mechanism for use in accord with the present invention.

FIG. 8 shows a refill cassette with an alternative indexing mechanism herein. The mechanism comprises a number of recesses 748a, 748b located on an arm of the indexing lever 740 which protrudes into the cassette 730. The recesses 748a, 748b are shaped and sized to engage the pockets in a blister strip (not shown). When the indexing lever 740 is moved by the patient the blister strip is indexed by one pocket. Resetting the lever 740 back to its rest position results in the lever 740 disengaging the strip temporarily and then reengaging it one pocket further along. This mechanism has the advantage in that it is simple and reduces the number of components required within the device, therefore reducing both the overall cost of the device components and the cost of assembling it.

Figure 9A:
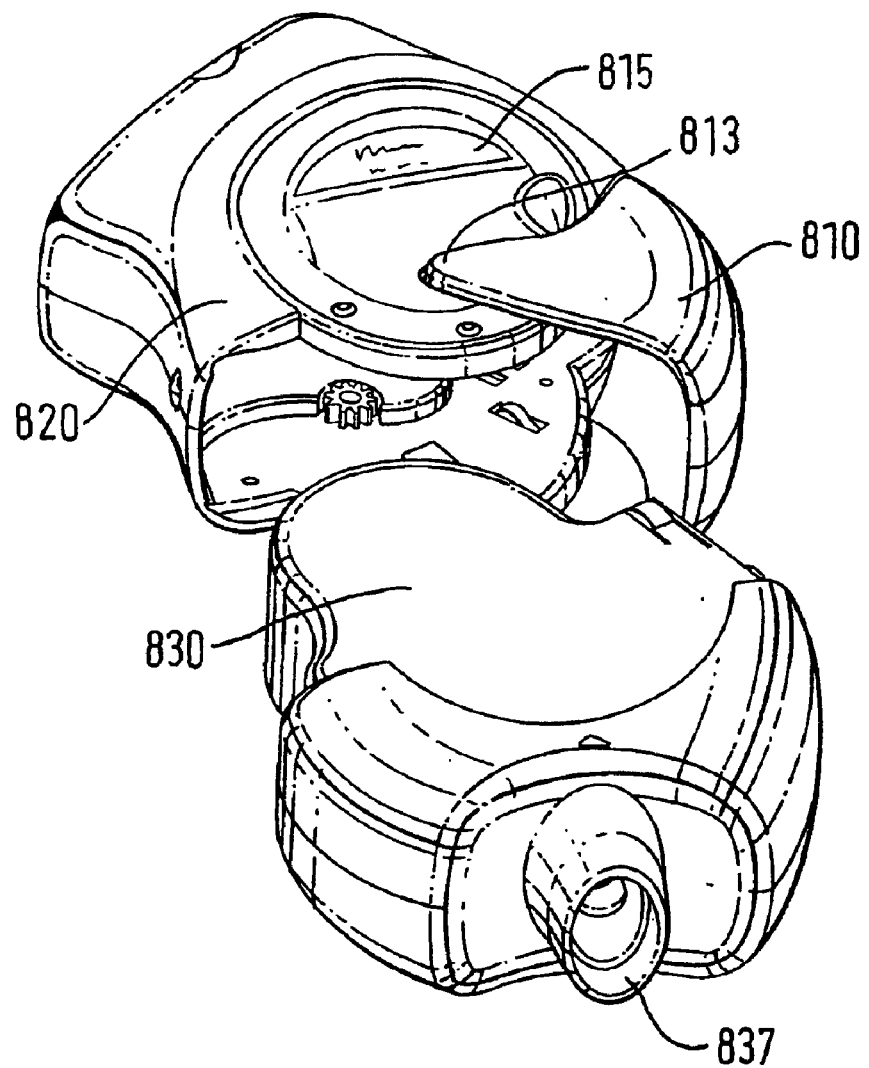
FIG. 9a shows a perspective view of a medicament dispenser, in the form of a holder/body and a refill cassette, in accord with the invention with the cassette removed from the holder/body.
Figure 9C:
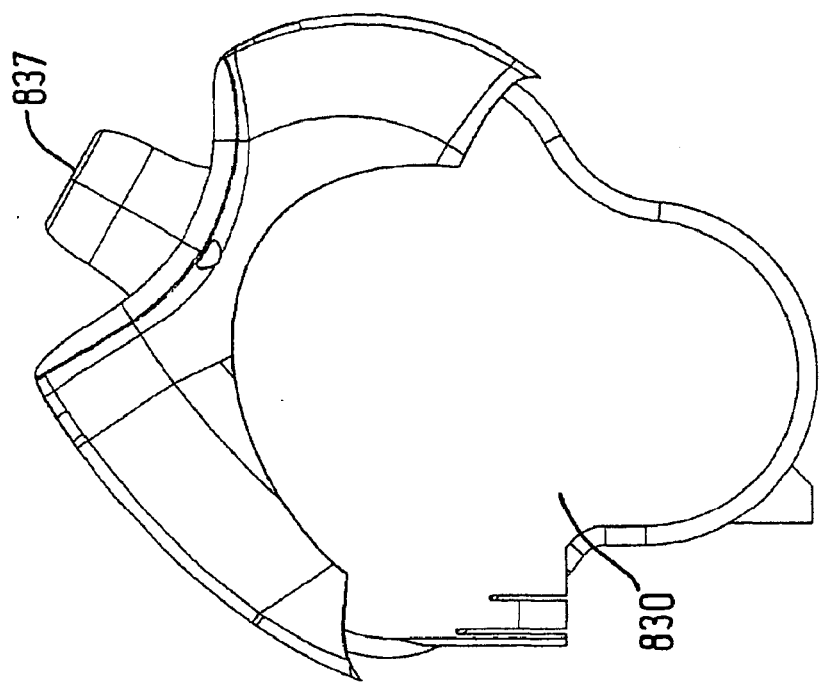
Figure 9B:
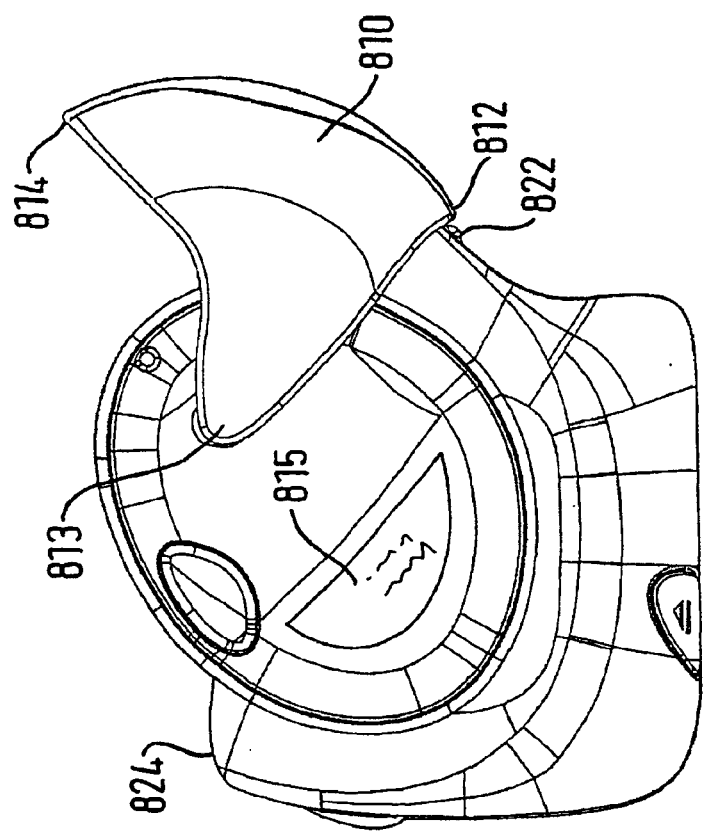

FIGS. 9a to 9c illustrate a medicament dispenser according to another aspect of the present invention. The medicament dispenser comprises a body cover 810, a holder 820, refill cassette 830 and electronic display 815. The holder 820 is shaped to fit snugly inside body 810 to a point on the body 813 about which it rotates. Stops 822, 824 protrude from the holder 820 to prevent the holder 820 from rotating more than about 1100 relative to the body cover 810. The stops 822, 824 also provide two defined positions of the holder 820 within the body cover 810. One position is defined by stop 822 meeting with body edge 812 and the other position defined by stop 824 meeting with body edge 814 when the holder has been rotated relative to the body. The holder 820 forms a shell into which the refill cassette 830 snugly fits.

The refill cassette 830 comprises a shell body containing the medicament carrier (not shown) and an internal mechanism for opening the carrier (not shown) for the medicament to be accessed. The refill cassette 830 has a mouthpiece 837 arranged such that in use, the mouthpiece 837 protrudes from the holder 820 but the bulk of the cassette 830 is contained within the holder 820.

Figure 10:
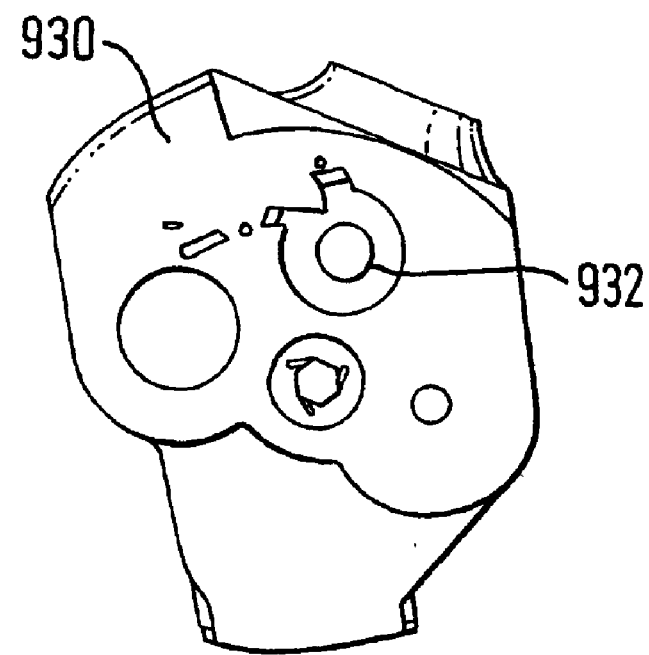
FIG. 10 shows a perspective view of a medicament dispenser, in the form of a holder/body and a refill cassette with integral mouthpiece, in accord with the invention with the cassette removed from the holder/body.
Figure 10:
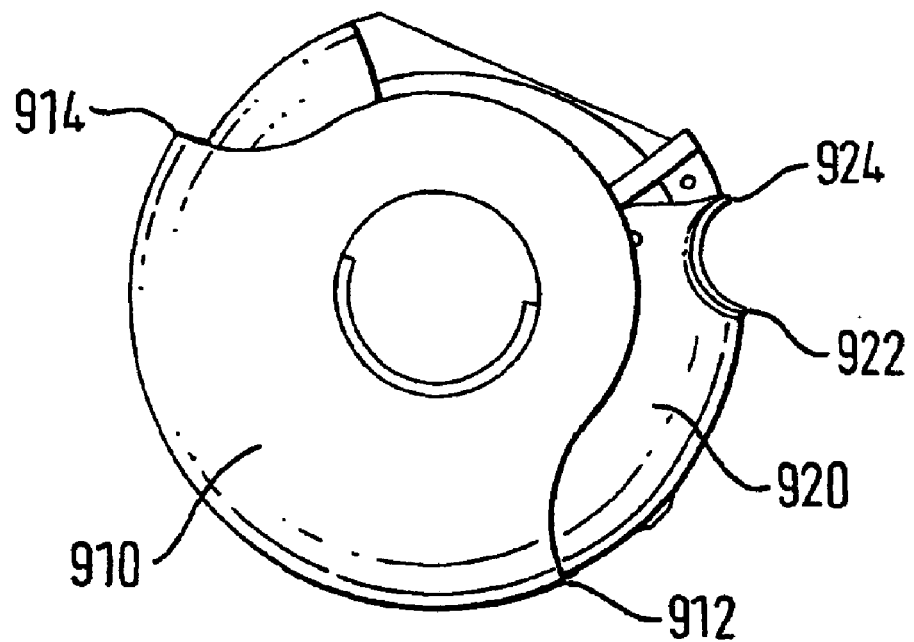

FIG. 10 illustrates a further medicament dispenser according to another aspect of the present invention. The medicament dispenser comprises a body cover 910, a holder 920 and refill cassette 930. The holder 920 is shaped to fit snugly inside body 910 to a point on the body (not shown) about which it rotates. Stops 922, 924 protrude from the holder 920 to prevent the holder 920 from rotating more than about 180° relative to the body cover 910. The stops 922, 924 also provide two defined positions of the holder 920 within the body cover 910. One position is defined by stop 922 meeting with body edge 912 and the other position defined by stop 924 meeting with body edge 914 when the holder has been rotated relative to the body. The holder 920 forms a shell into which the refill cassette 930 snugly fits by way of a side loading engagement.

The refill cassette 930 comprises a shell body containing the medicament carrier (not shown) and an internal mechanism 932 for opening the carrier for the medicament to be accessed. The refill cassette 930 has a mouthpiece 937 arranged such that in use, the mouthpiece 937 protrudes from the holder 920 but the bulk of the cassette 930 is contained within the holder 920.

Figure 11:
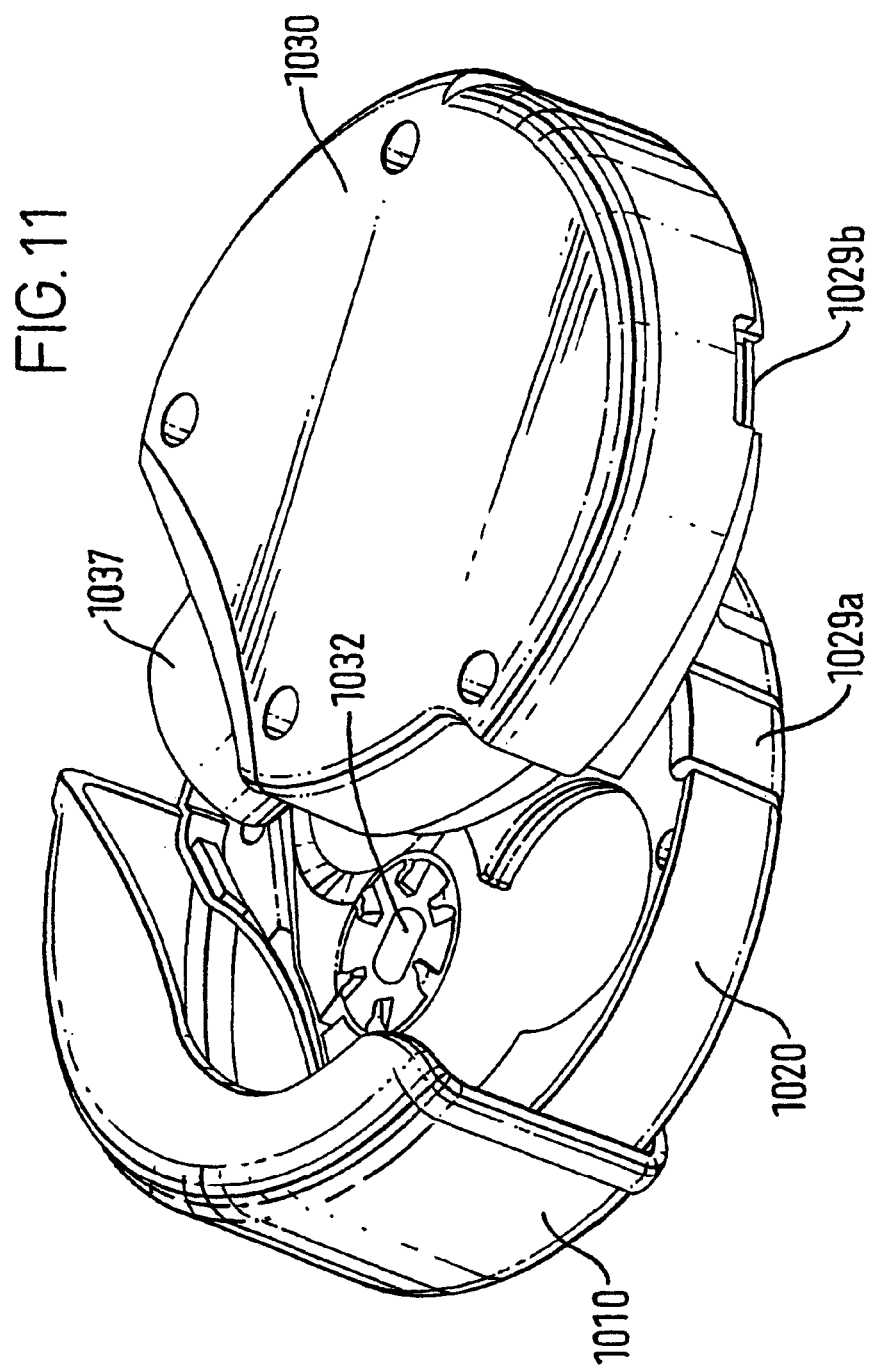
FIG. 11 shows a perspective view of a medicament dispenser, in the form of a holder/body and a refill cassette with integral mouthpiece, in accord with the invention with the cassette removed from the holder/body.

FIG. 11 illustrates a further medicament dispenser according to another aspect of the present invention. The medicament dispenser comprises a body cover 1010, a holder 1020 and refill cassette 1030. The holder 1020 is shaped to fit snugly inside body 1010 to a point on the body (not shown) about which it rotates. The holder 1020 forms a landing station with which the refill cassette 1030 snugly engages by way of a face-to-face snap-fit 1029a, 1029b engagement. When so engaged, the holder 1020 and the cassette 1030 in combination form the bulk of the overall 'body form' of the medicament dispenser.

The refill cassette 1030 comprises a shell body containing the medicament carrier (not shown) and an internal mechanism 1032 for opening the carrier for the medicament to be accessed. The refill cassette 1030 has a mouthpiece 1037 arranged such that in use, the mouthpiece 1037 protrudes from the dispenser.

It may be appreciated that any of the parts of the dispenser or actuator which contact the medicament suspension may be coated with materials such as fluoropolymer materials (e.g. PTFE or FEP) which reduce the tendency of medicament to adhere thereto. Any movable parts may also have coatings applied thereto which enhance their desired movement characteristics. Frictional coatings may therefore be applied to enhance frictional contact and lubricants (e.g. silicone oil) used to reduce frictional contact as necessary.

The medicament dispenser of the invention is suitable for dispensing medicament, particularly for the treatment of respiratory disorders such as asthma and chronic obstructive pulmonary disease (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg s the sodium salt), ketotifen or nedocromil (eg as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone eg as the furoate ester), ciclesonide, triamcinolone (eg as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy) acetyl] amino}pentanoyl)amino] propanoic acid (e.g as free acid or potassium salt), diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (eg as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. A medicament dispenser for dispensing medicament comprising:
   a body;
   a holder, shaped to fit within said body and movable relative to the body; and
   receivable by said holder, a cassette containing a medicament carrier,
   wherein movement of the holder relative to the body results in movement of the cassette between a first position and a second position such that the cassette is reversibly removable from the holder when the cassette is in the second position.

2. A medicament dispenser according to claim 1, wherein the first position comprises a dispensing position.

3. A medicament dispenser according to claim 2, wherein the second position comprises a non-dispensing position.

4. A medicament dispenser according to any of claim 1, wherein the holder and body include attachment means to attach the holder to the body.

5. A medicament dispenser according to claim 4, wherein said attachment means comprise a pin and hole system.

6. A medicament dispenser according to any of claim 1, wherein the holder is pivotally movable relative to the body.

7. A medicament dispenser according to any of claim 1, wherein the holder is rotationally movable relative to the body.

8. A medicament dispenser according to any of claim 1, wherein the holder is slidably movable relative to the body.

9. A medicament dispenser according to any of claim 1, wherein the holder additionally comprises a stop to limit movement of the holder relative to the body.

10. A medicament dispenser according to claim 9, wherein two distinct stop positions are defined corresponding to the dispensing and non-dispensing positions respectively.

11. A medicament dispenser according to any of claim 1, wherein the holder additionally comprises a retainer for retaining the cassette therewithin.

12. A medicament dispenser according to claim 11, wherein the retainer comprises a catch.

13. A medicament dispenser according to any of claim 1, wherein the holder includes a guide for guiding the insertion of the cassette into the holder.

14. A medicament dispenser according to any of claim 1, wherein the cassette additionally comprises a dispensing outlet.

15. A medicament dispenser according to claim 14, wherein the dispensing outlet is retractable.

16. A medicament dispenser according to any of claim 1, wherein the cassette is shaped to prevent incorrect insertion into the holder.

17. A medicament dispenser according to any of claim 1, wherein the medicament carrier is in a form selected from the group consisting of capsule; a tablet carrier; an aqueous container; an aerosol container; and a dry powder container.

18. A medicament dispenser according to any of claim 17, wherein the medicament carrier comprises a container for a reservoir of dry powder.

19. A medicament dispenser according to claim 17, wherein the medicament carrier comprises an elongate carrier.

20. A medicament dispenser according to claim 19, wherein the medicament carrier comprises an elongate strip formed from a base sheet having a plurality of recesses spaced along its length and a lid sheet peelably sealed in superposed relationship thereto to define a plurality of blisters, each for containing medicament therein.

21. A medicament dispenser according to any of claim 1, wherein the cassette additionally comprises an internal mechanism for acting on the medicament carrier there within.

22. A medicament dispenser according to claim 21, wherein the internal mechanism comprises an indexer for indexing the medicament carrier.

23. A medicament dispenser according to claim 21, wherein the internal mechanism comprises a mover for moving the medicament carrier.

24. A medicament dispenser according to claim 23, wherein the internal mechanism comprises access means for accessing the medicament carrier.

25. A medicament dispenser according to any of claim 21, wherein the body or holder additionally comprises a drive mechanism for driving at least part of the internal mechanism of the cassette.

26. A medicament dispenser according to claim 25, wherein the drive mechanism is a manual drive mechanism.

27. A medicament dispenser according to claim 25, wherein the drive mechanism is a powered drive mechanism.

28. A medicament dispenser according to any of claim 21, wherein said internal mechanism comprises:
   a) an opening station for receiving a medicament carrier of the cassette, said medicament carrier having plural individual medicament containers;
   b) an indexer for indexing an individual medicament container of the medicament carrier for receipt by said opening station;
   c) an opener for opening said indexed individual medicament container; and
   d) a dispensing outlet, positioned to communicate with said opened container.

29. A medicament dispenser according to claim 28, wherein the medicament carrier comprises a peelable blister strip comprising a base sheet and lid sheet which may be peeled apart to uncover a pocket in the base sheet and the opener comprises peeling means for engaging said base sheet and said lid sheet for peeling apart the base sheet and lid sheet.

30. A medicament dispenser according to claim 29, wherein said peeling means includes lid driving means for pulling the lid sheet apart from the base sheet.

31. A medicament dispenser according to any of claim 28, wherein said indexer comprises a rotatable index wheel having recesses therein, said index wheel engaging the medicament carrier such that one or more of said recesses each receive an individual medicament container.

32. A medicament dispenser according to any of claim 28, wherein the indexer comprises an index ratchet which is moveable between a locked position whereby said ratchet engages a pocket on said medicament carrier and prevents further peeling thereof, and a release position allowing free movement of said medicament carrier.

33. A medicament dispenser according to claim 32, wherein actuation of the medicament dispenser actuates the lid driving means of the opener to release said index ratchet from said medicament carrier to allow peeling thereof.

34. A medicament dispenser according to any of claim 30, wherein said lid driving means comprise a wheel on which the lid sheet is wound up.

35. A medicament dispenser according to claim 34, wherein said wheel comprises a plurality of resiliently flexible arms each extending therefrom at an angle with respect to a radius.

36. A medicament dispenser according to any of claim 30, wherein said lid driving means comprises a mangle.

37. A medicament dispenser according to any of claim 30, wherein said lid driving means comprises a roller.

38. A medicament dispenser according to any of claim 30, wherein the lid driving means comprise a lid spool on which the lid sheet is wound up.

39. A medicament dispenser according to any of claim 1, wherein the cassette comprises a first chamber for holding the medicament carrier when charged with medicament and a second chamber to receive the medicament carrier after release of medicament therefrom.

40. A medicament dispenser according to claim 39 wherein said first chamber and said second chamber are separated by a wall.

41. A medicament dispenser according to claim 40, wherein said wall is movable to adjust the respective size of the first and second chambers.

42. A medicament dispenser according to any of claim 1, additionally comprising an actuation counter for counting the number of actuations of the indexer.

43. A medicament dispenser according to any of claim 1, additionally comprising a dose release counter for counting the number of dose releases from the cassette.

44. A medicament dispenser according to any of claim 1, additionally comprising an electronic data management system.

45. A medicament dispenser according to claim 44, additionally comprising in association with the body, a first transceiver for transmitting and receiving data and in association with the medicament carrier, a second transceiver for transmitting and receiving data, wherein data is transferable in two-way fashion from the first transceiver to the second transceiver.

46. A medicament dispenser according to any of claim 1, wherein at least a portion of the body is shaped for ease of grip by the user.

47. A medicament dispenser according to any of claim 1, wherein the holder includes a thumb or finger grip.

48. A medicament dispenser according to any of claim 1, wherein operation of the dispenser may be performed with one hand.

49. A medicament dispenser according to any of claim 1, wherein said medicament carrier is carrying medicament.

50. A medicament dispenser according to claim 49, wherein the medicament is selected from the group consisting of albuterol, salmeterol, fluticasone propionate and beclomethasone dipropionate and salts or solvates thereof and any combination thereof.

51. A medicament dispenser according to claim 50, wherein the medicament comprises salmeterol xinafoate and fluticasone propionate.

52. A medicament dispenser according to any of claim 49, wherein the medicament additionally comprises an excipient.

53. A medicament dispenser according to claim 52, said excipient is a sugar.

54. Use of a medicament dispenser according to any of claim 49 for dispensing medicament.

55. A medicament dispenser in kit of parts form comprising
    (a) a body; a holder, shaped to fit within said body and movable relative to said body; and within said holder a receiving station for receipt of a cassette; and
    (b) a cassette containing a medicament carrier,
    wherein the cassette is receivable by the receiving station and movement of the holder relative to the body results in movement of the cassette between a first position and a second position such that the cassette is reversibly removable from the receiving station when the cassette is in the second position.

56. A kit of parts according to claim 55, wherein the cassette includes an internal mechanism for acting on said medicament carrier.

57. A kit of parts according to claim 56, wherein the internal mechanism comprises an indexer for indexing the medicament carrier.

58. A kit of parts according to claim 56, wherein the internal mechanism comprises a mover for moving the medicament carrier.

59. A kit of parts according to claim 56, wherein the internal mechanism comprises access means for accessing the medicament carrier.

60. A kit of parts according to any of claim 56, wherein the body or holder additionally comprises a drive mechanism for driving at least part of the internal mechanism of the cassette.

61. A kit of parts according to claim 60, wherein the drive mechanism is a manual drive mechanism.

62. A kit of parts according to claim 61, wherein the drive mechanism is a powered drive mechanism.

* * * * *

UNITED STATES PATENT AND TRADEMARK OFFICE
CERTIFICATE OF CORRECTION

PATENT NO. : 6,880,722 B2
DATED : April 19, 2005
INVENTOR(S) : Gregor John McLennan Anderson et al.

It is certified that error appears in the above-identified patent and that said Letters Patent is hereby corrected as shown below:

Title page,
Item [56], References Cited, FOREIGN PATENT DOCUMENTS, "GB 2240758" should read -- GB 2340758 --.

Signed and Sealed this

Twentieth Day of September, 2005

JON W. DUDAS
*Director of the United States Patent and Trademark Office*